United States Patent [19]
Hendrickx et al.

[11] Patent Number: 6,100,262
[45] Date of Patent: Aug. 8, 2000

[54] (2-MORPHOLINYLMETHYL) BENZAMIDE DERIVATIVES

[75] Inventors: Marie-Louise Hendrickx, Turnhout; Kurt Godfried Cornelius Emile Van Daele, Borgerhout; Peter Jules Victor Van Daele, Grimbergen; Glenn Kurt Ludo Van Daele, Turnhout; Frans Maria Alfons Van den Keybus, Essen; Marc Gustaaf Celine Verdonck, Gierle, all of Belgium

[73] Assignee: Janssen Pharmaceutica, NV., Beerse, Belgium

[21] Appl. No.: 09/401,729

[22] Filed: Sep. 22, 1999

Related U.S. Application Data

[63] Continuation of application No. 08/945,740, filed as application No. PCT/EP96/02141, May 15, 1996, abandoned.

[30] Foreign Application Priority Data

May 23, 1995 [EP] European Pat. Off. ............ 95 201 350

[51] Int. Cl.[7] ...................... A61K 31/535; C07D 265/30; C07D 413/06
[52] U.S. Cl. .................................... 514/237.8; 514/235.8; 544/121; 544/130; 544/141; 544/165
[58] Field of Search ................................... 544/121, 163; 514/237.8

[56] References Cited

FOREIGN PATENT DOCUMENTS 0 243 959  11/1987  European Pat. Off. .
95 26953   10/1995  WIPO .

OTHER PUBLICATIONS

Chemical and Pharmaceutical Bulletin, vol. 40, No. 3, 1992, Tokyo JP, pp. 652–660, XP002012408; S. Kato et al.: "Novel benzamides as selective and potent gastrokinetic agents".

Primary Examiner—Robert W. Ramsuer
Attorney, Agent, or Firm—Ellen Ciambrone Coletti

[57] ABSTRACT

The present invention concerns novel (2-morpholinylmethyl)benzamide derivatives having the formula

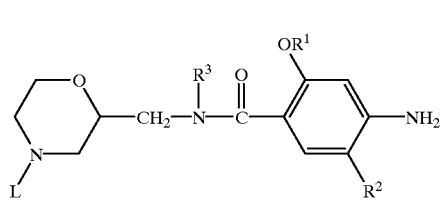

(I)

the N-oxide forms, the pharmaceutically acceptable addition salts and the stereochemically isomeric forms thereof, wherein $R^1$ is $C_{1-6}$alkyl, $C_{2-6}$alkenyl or $C_{2-6}$alkynyl; $R^2$ is hydrogen, halo or $C_{1-6}$alkylsulfonylamino; $R^3$ is hydrogen or $C_{1-6}$alkyl; L is a radical of formula $R^4$—C(=O)—Alk— (a); $R^5$—C(=O)—N($R^6$)—Alk— (b); or $R^7$—C(=O)—O—Alk— (c); wherein each Alk is independently $C_{1-12}$alkanediyl; $R^4$ is hydrogen, hydroxy, $C_{1-6}$alkyl, $C_{1-6}$alkyloxy, amino, mono- or di($C_{1-6}$alkyl)amino or an optionally substituted heterocyclic ring; $R^5$ and $R^7$ each independently are hydrogen, $C_{1-6}$alkyl, $C_{1-6}$alkyloxy, amino, mono- or di($C_{1-6}$alkyl)amino or an optionally substituted heterocyclic ring; $R^6$ is hydrogen or $C_{1-6}$alkyl; and aryl is phenyl or phenyl substituted with 1, 2 or 3 substituents selected from halo, $C_{1-6}$alkyl or $C_{1-6}$alkyloxy. It further relates to pharmaceutical compositions comprising them, processes for preparing said compounds and compositions, and the use thereof as a medicine, in particular in the conditions involving a decreased gastric emptying.

25 Claims, No Drawings

(2-MORPHOLINYLMETHYL) BENZAMIDE DERIVATIVES

CROSS REFERENCE TO RELATED APPLICATIONS

This application is a continuation application of U.S. Ser. No. 08/945,740, now abandoned filed Sep. 28, 1998, which application is the national stage of application No. PCT/EP 96/02141, filed on May 15, 1996, which application claims priority from EP 95.201.350.6, filed on May 23, 1995.

The present invention concerns novel (2-morpholinylmethyl)benzamide derivatives having favourable gastrointestinal motility stimulating properties, in particular they accelerate the gastric emptying. It further relates to pharmaceutical compositions comprising them, processes for preparing said compounds and compositions, and the use thereof as a medicine.

EP-A-0,243,959, published on Nov. 4, 1987, discloses a number of (2-morpholinylalkyl)benzamide derivatives as gastrointestinal motility enhancing agents having less adverse effects on the central nervous system than metoclopramide.

The compounds of the present invention differ from the prior art compounds in that the substituent on the nitrogen of the morpholinyl moiety, i.e. substituent L in formula (I), invariably contains a carbonyl function. The present compounds unexpectedly show favourable gastrointestinal motility stimulating properties. More in particular, they accelerate the gastric emptying.

The present invention concerns novel (2-morpholinylmethyl)benzamide derivatives having the formula

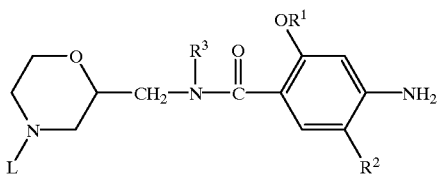

(I)

the N-oxide forms, the pharmaceutically acceptable addition salts and the stereochemically isomeric forms thereof, wherein $R^1$ is $C_{1-6}$alkyl, $C_{2-6}$alkenyl or $C_{2-6}$alkynyl;
$R^2$ is hydrogen, halo or $C_{1-6}$alkylsulfonylamino;
$R^3$ is hydrogen or $C_{1-6}$alkyl;
L is a radical of formula

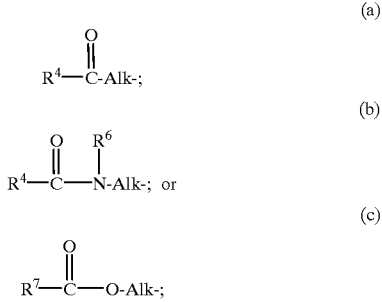

wherein
each Alk independently is $C_{1-12}$alkanediyl;

$R^4$ is hydrogen; hydroxy; $C_{1-6}$alkyl; $C_{1-6}$allyloxy; amino; mono- or di($C_{1-6}$alkyl)amino; 1-piperidinyl; 1-piperidinyl substituted with 1 or 2 substituents selected from $C_{1-6}$alkyl, $C_{1-6}$alkyloxy, amino, mono- or di($C_{1-6}$alkyl)amino or aryl; 1-pyrrolidinyl; 1-pyrrolidinyl substituted with 1 or 2 substituents selected from $C_{1-6}$alkyl, $C_{1-6}$alkyloxy, amino, mono- or di($C_{1-6}$alkyl)amino or aryl; 1-piperazinyl; 1-piperazinyl substituted with 1 or 2 substituents selected from $C_{1-6}$alkyl, $C_{1-6}$alkyloxy, amino, mono- or di($C_{1-6}$alkyl)amino or aryl; hexahydro-1H-diazepin-1-yl or hexahydro-1H-diazepin-1-yl substituted with 1 or 2 substituents selected from $C_{1-6}$alkyl, $C_{1-6}$alkyloxy, amino, mono- or di($C_{1-6}$alkyl)amino or aryl;

$R^5$ and $R^7$ each independently are hydrogen; $C_{1-6}$alkyl; $C_{1-6}$alkyloxy; amino; mono- or di($C_{1-6}$alkyl)amino; 1-piperidinyl; 1-piperidinyl substituted with 1 or 2 substituents selected from $C_{1-6}$alkyl, $C_{1-6}$alkyloxy, amino, mono- or di($C_{1-6}$alkyl)amino or aryl; 1-pyrrolidinyl; 1-pyrrolidinyl substituted with 1 or 2 substituents selected from $C_{1-6}$alkyl, $C_{1-6}$alkyloxy, amino, mono- or di($C_{1-6}$alkyl)amino or aryl; 1-piperazinyl; 1-piperazinyl substituted with 1 or 2 substituents selected from $C_{1-6}$alkyl, $C_{1-6}$alkyloxy, amino, mono- or di($C_{1-6}$alkyl)amino or aryl; hexahydro-1H-diazepin-1-yl or hexahydro-1H-diazepin-1-yl substituted with 1 or 2 substituents selected from $C_{1-6}$alkyl, $C_{1-6}$alkyloxy, amino, mono- or di($C_{1-6}$alkyl)amino or aryl;

$R^6$ is hydrogen or $C_{1-6}$alkyl; and aryl is phenyl or phenyl substituted with 1, 2 or 3 substituents selected from halo, $C_{1-6}$alkyl or $C_{1-6}$alkyloxy.

As used in the foregoing definitions and hereinafter, substitution on the 1-piperazinyl ring may be on the nitrogen atom in the 4 position or on any carbon atom; substitution on the hexahydro-1H-diazepin-1-yl ring may be on the nitrogen atom in the 4 position or on any carbon atom; halo is generic to fluoro, chloro, bromo and iodo; $C_{1-6}$alkyl defines straight and branched saturated hydrocarbon radicals having from 1 to 6 carbon atoms such as, for example, methyl, ethyl, propyl, butyl, 1-methylethyl, 2-methylpropyl, pentyl, hexyl and the like; $C_{2-6}$alkenyl defines straight or branched hydrocarbon radicals having one double bond and having from 2 to 6 carbon atoms such as, for example, ethenyl, 2-propenyl, 3-butenyl, 2-butenyl, 2-pentenyl, 3-methyl-2-butenyl and the like; $C_{2-6}$alkynyl defines straight or branched hydrocarbon radicals having one triple bond and having 2 to 6 carbon atoms such as, for example, ethynyl, 2-propynyl, 3-butynyl, 2-butynyl, 2-pentynyl, 3-methyl-2-butynyl and the like; $C_{1-6}$alkanediyl defines bivalent straight or branched hydrocarbon radicals containing from 1 to 6 carbon atoms such as, for example, 1,2-ethanediyl, 1,3-propanediyl, 1,4butanediyl, 1,5-pentanediyl, 1,6hexanediyl and the branched isomers thereof; $C_{1-12}$alkanediyl defines $C_{1-6}$alkanediyl and the higher homologues thereof having 7 to 12 carbon atoms such as, for example, 1,7-heptanediyl, 1,8-octanediyl, 1,9-nonanediyl, 1,10-decanediyl, 1,11-undecanediyl, 1,12-dodecanediyl and the branched isomers thereof.

The pharmaceutically acceptable addition salts as mentioned hereinabove are meant to include the therapeutically active non-toxic base and acid addition salt forms which the compounds of formula (I) are able to form. The acid addition salt forms can conveniently be obtained by treating the free base form of a compound of formula (I) with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely the acid addition salt form can be converted by treatment with alkali into the free base form.

The compounds of formula (I) containing an acidic proton may also be converted into their non-toxic base, i.e. metal or amine, addition salt forms by treatment with appropriate organic and inorganic bases. Appropriate base salt forms comprise, for example, the ammonium salts, the alkali and earth alkaline metal salts, e.g. the lithium, sodium, potassium, miagniesium, calcium salts and the like, salts with organic bases, e.g. the benzathine, N-methyl-D-glucamine, hydrabamine salts, and salts with amino acids such as, for example, arginine, lysine and the like. Conversely the base addition salt form can be converted by treatment with acid into the free acid form.

The term addition salt as used hereinabove also comprises the solvates which the compounds of formula (I) as well as the salts thereof, are able to form. Such solvates are for example hydrates, alcoholates and the like.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic saturated radicals may have either the cis- or trans-configuration. Compounds of formula (I) wherein $R^1$ is $C_{2-6}$alkenyl may occur as mixtures of E- and Z-forms, or as pure E-forms or pure Z-forms. Stereochemically isomeric forms of the compounds of formula (I) are obviously intended to be embraced within the scope of this invention.

Some of the compounds of formula (I) may also exist in their tautomeric form. Such forms although not explicitly indicated in the above formula are intended to be included within the scope of the present invention.

The N-oxide forms of the compounds of formula (I) are meant to comprise those compounds of formula (I) wherein one or several nitrogen atoms are oxidized to the so-called N-oxide, particularly those N-oxides wherein the morpholine-nitrogen is N-oxidized.

Whenever used hereinafter, the term compounds of formula (I) is meant to also include the N-oxide forms, the pharmaceutically acceptable addition salts and all stereoisomeric forms.

Particular groups of compounds of formula (I) are those wherein one or more of the following restrictions apply:

a) $R^1$ is $C_{1-6}$alkyl, preferably methyl;
b) $R^2$ is halo, preferably chloro;
c) $R^3$ is hydrogen;
d) L is a radical of formula (a);
e) Alk is $C_{1-6}$alkanediyl; preferably 1,3-propanediyl, 1,4-butanediyl or 1,5-pentanediyl.

Preferred compounds are those compounds of formula (I) wherein $R^1$ is methyl, $R^2$ is chloro, $R^3$ is hydrogen, Alk is 1,3-propanediyl, 1,4-butanediyl or 1,5-pentanediyl, and L is a radical of formula (a) wherein $R^4$ is $C_{1-6}$alkyl, di($C_{1-6}$alkyl)amino or 1-pyrrolidinyl.

Most preferred compounds are
2-[[(4-amino-5-chloro-2-methoxybenzoyl)amino]methyl]-N,N-diethyl-4-morpholine-butanamide;
4-amino-5-chloro-2-methoxy-N-[[4-[4-oxo-4-(1-pyrrolidinyl)butyl]-2-morpholinyl]-methyl]benzamide;
the pharmaceutically acceptable addition salts and the stereochemically isomeric forms thereof.

Whenever used hereinafter, $R^1$ to $R^3$ and L are as defined under formula (I) unless otherwise indicated.

In the following preparations, the reaction products may be isolated from the reaction mixture and, if necessary, further purified according to methodologies generally known in the art such as, for example, extraction, distillation, crystallization, trituration and chromatography.

The compounds of formula (I) can generally be prepared according to the mehods described in EP-A-0,243,959.

In particular, compounds of formula (I) may be prepared by N-alkylating a morpholine derivative of formula (II) with an intermediate of formula (III) wherein W is a reactive leaving group such as, for example, halo, e.g. chloro, bromo or iodo, or a sulfonyloxy group, e.g. methanesulfonyloxy, toluenesulfonyloxy and the like leaving groups.

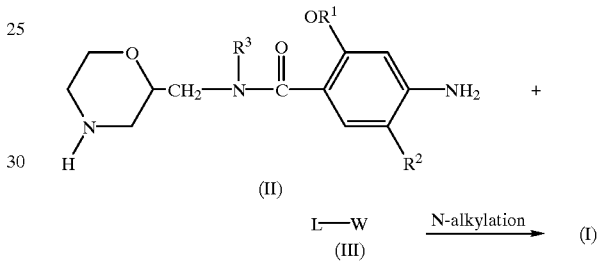

Said N-alkylation may conveniently be performed in a reaction-inert solvent such as, for example, N,N-dimethylforinamide or methyl isobutyl keton, in the presence of a suitable base such as, for example, sodium carbonate or diethylethanamine, which may be utilized to pick up the acid which is liberated during the course of the reaction. In some instances, the addition of an iodide salt, preferably an alkali metal iodide, or a crown ether, e.g. 1,4,7,10,13,16-hexaoxacyclooctadecane and the like, may be appropriate. Stirring and elevated temperatures may enhance the rate of the reaction. Additionally, it may be advantageous to conduct said N-alkylation under an inert atmosphere such as, for example, oxygen-free argon or nitrogen gas.

The compounds of formula (I) may further be prepared by converting compounds of formula (I) into each other according to art-known group transformation reactions. The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

The reagents and intermediates of formula (II) and (III) required for the synthesis of the compounds of the present invention are either commercially readily available, or may be prepared according to known procedures. For example, EP-A-0,243,959 describes the preparation of some of the intermediates of formula (II), and FP-A-0,309,043, published on Mar. 29, 1989, describes the preparation of some of the intermediates of formula (III).

The compounds of formula (I) the N-oxide forms, the pharmaceutically acceptable addition salts and possible stereoisomeric forms thereof possess favourable gastrointestinal motility stimulating properties. In particular, the present compounds show significant motility enhancing effects on the gastric emptying. The latter property can be evidenced by the results obtained in the "Gastric emptying of a liquid meal in rats"-test described hereinafter, and may further be evidenced by the "Gastric emptying of an acaloric meal in conscious dog after administration of lidamidine"-test.

In addition, most of the present compounds of formula (I), the N-oxide forms, the pharmaceutically acceptable addition salts and possible stereoisomeric forms thereof show little or no receptor-binding affinity with serotonergic-5HT, and serotonergic-5HT$_2$ receptors and have little or no dopaminergic antagonistic activity.

In view of their useful gastrointestinal motility enhancing properties the subject compounds may be formulated into various forms for administration purposes.

As appropriate pharmaceutical compositions there may be cited all compositions usually employed for systemically administering drugs. To prepare the pharmaceutical compositions of this invention, a therapeutically effective amount of the particular compound, optionally in addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Addition salts of compounds of formula (I) due to their increased water solubility over the corresponding free base or acid form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

In view of the capability of the compounds of the present invention to stimulate the motility of the gastrointestinal system and, in particular their capacity to accelarate the gastric emptying, the subject compounds are useful to normalize or to improve the gastric and intestinal emptying in subjects suffering from a disturbed motility, e.g. a decreased peristalsis of the oesophagus and/or stomach and/or small and/or large intestine.

In view of the utility of the compounds of formula (I), it follows that the present invention also provides a method of treating warm-blooded animals suffering from motility disorders of the gastrointestinal system such as, for example, oesophagitis, gastroparesis, flatulent dyspepsia, non-ulcer dyspepsia, pseudo-obstruction, impaired colonic transit and the like disorders. Said method comprising the systemic administration of an effective gastrointestinal stimulating amount of a compound of formula (I) to warm-blooded animals. Hence, the use of a compound of formula (I) as a medicine is provided, and in particular the use of a compound of formula (I) for the manufacture of a medicine for treating conditions involving a decreased gastrointestinal motility.

Those of skill in the treatment of such motility disorders could determine the effective stimulating amount from the test results presented hereinafter. An daily effective amount would be from about 0.1 mg/kg to about 40 mg/kg body weight, more preferably from about 0.5 mg/kg to about 5 mg/kg body weight. A method of treatment may also include administering the active ingredient on a regimen of between two to four intakes per day.

The following examples are intended to illustrate and not to limit the scope of the present invention.

EXPERIMENTAL PART

A. Preparation of the Compounds of Formula (I)

Example 1

A mixture of 4-chloro-N,N-diethylbutanamide (2.16 g), 4-amino-5-chloro-2-methoxy-N-(2-morpholinylmethyl) benzenamide (3 g), prepared following the procedure as described in EP-A-0,243,959, and sodium carbonate (1.58 g) in N,N-dimethyl-formamide (90 ml) was stirred for 48 hours at 70° C. The solvent was evaporated and water was added to the residue. This mixture was extracted twice with dichloromethane and the combined extracts were washed with water, dried, filtered and the solvent evaporated. The residue was purified by column chromatography over silica gel (eluent: $CHCl_3/CH_3OH$ 95/5). The first fraction was collected and the solvent was evaporated. The residue was converted into the hydrochloric salt in 2-propanol and diisopropyl ether. The salt was filtered off and crystallized from acetonitrile. The precipitate was filtered off and dried, yielding 1.43 g (30.4%) of (±)-2-[[(4-amino-5-chloro-2-methoxybenzoyl)amino]methyl]-N,N-diethyl4-morpholine-butanamide monohydrochloride. hemihydrate (compound 1; mp. 122.2° C.).

In a similar way, the compounds in table 1 were prepared.

TABLE 1

[Structure: morpholine-CH2-NH-C(=O)-benzene ring with OCH3, NH2, Cl substituents; L on morpholine N]

| Compound No. | L | Physical data (mp. in °C.) |
|---|---|---|
| 1 | N,N-diethylbutanamide | (±)/HCl.½H₂O/122.2 |
| 2 | 4-oxopentyl | (±)/129.2 |
| 3 | 4-(4-methyl-1-piperazinyl)-5-oxopentyl | (±)/2HCl.½H₂O/257.4 |
| 4 | 4-oxo-4-(1-piperidinyl)butyl | (±)/118.7 |
| 5 | 2-(4-methyl-l-piperazinyl)-2-oxoethyl | (±)/H₂O/118.7 |
| 6 | 6-(4-methyl-1-piperazinyl)-6-oxohexyl | (±)/123.8 |
| 7 | 4-oxo-4-(4-phenyl-1-piperazinyl)butyl | (±)/224.2 |
| 8 | 4-oxo-4-(1-pyrrolidinyl)butyl | (±)/120.0 |

B. Pharmacological Example

Example 2

"Gastric Emptying of a Liquid Meal in Rats" Test

Gastric emptying was measured in rats according to a modified version of a method originally devised by Reynell and Spray (J. Physiol., 131,452–456 (1956)). Rats were originally devised during 24 hours and isolated in individual cages. The test meal, which consisted of a warm suspension of 200 mg phenol red in 40 ml distilled water was given by oral intubation (0.4 ml/rat) half an hour after subcutaneous administration of a formula (I) or saline. The rats were sacrificed by cervical dislocation half an hour later. The stomach was then exposed by laparotomy, quickly ligated at the pylorus and cardia, and removed. The stomach was cut up, and its contents was extracted with 100 ml of 0.1 N sodium hydroxide. The phenol red content of this extract was assayed colorimetrically at 558 nm in a spectrophotometer. A mean value of 1.41 extinction units was obtained in saline-treated animals. Table 2 shows the mean extinction unit following test injections of 2.5 mg/kg test compound.

TABLE 2

| Compound number | mean extinction unit |
|---|---|
| 1 | 0.63 |
| 2 | 1.01 |
| 3 | 1.12 |
| 4 | 0.89 |
| 5 | 1.35 |
| 6 | 0.98 |
| 7 | 0.71 |
| 8 | 0.52 |

C. Composition Examples

"Active ingredient" (A.I.) as used throughout these examples relates to a compound of formula (I), a N-oxide form, a pharmaceutically acceptable addition salt or a stereochemically isomeric form thereof.

Example 3

Oral Solutions 9 g of methyl 4-hydroxybenzoate and 1 g of propyl 4-hydroxybenzoate are dissolved in 4 l of boiling purified water. In 3 l of this solution are dissolved first 10 g of 2,3-dihydroxybutanedioic acid and thereafter 20 g of the A.I. The latter solution is combined with the remaining part of the former solution and 12 l of 1,2,3-propanetriol and 3 l of sorbitol 70% solution are added thereto. 40 g of sodium saccharin are dissolved in 0.5 l of water and 2 ml of raspberry and 2 ml of gooseberry essence are added. The latter solution is combined with the former, water is added q.s. to a volume of 20 l providing an oral solution comprising 5 mg of the A.I. per teaspoonful (5 ml). The resulting solution is filled in suitable containers.

Example 4

Film-coated Tablets

Preparation of Tablet Core

A mixture of 100 g of the A.I., 570 g lactose and 200 g starch is mixed well and thereafter humidified with a solution of 5 g sodium dodecyl sulfate and 10 g polyvinylpyrrolidone in about 200 ml of water. The wet powder mixture is sieved, dried and sieved again. Then there are added 100 g microcrystalline cellulose and 15 g hydrogenated vegetable oil. The whole is mixed well and compressed into tablets, giving 10.000 tablets, each comprising 10 mg of the active ingredient.

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinylpyrrolidone and 30 ml of concen-trated colour suspension and the whole is homogenated. The tablet cores are coated with the thus obtained mixture in a coating apparatus.

Example 5

Injectable Solution 1.8 g methyl 4-hydroxybenzoate and 0.2 g propyl 4-hydroxybenzoate were dissolved in about 0.5 l of boiling water for injection. After cooling to about 50° C. there were added while stirring 4 g lactic acid, 0.05 g propylene glycol and 4 g of the A.I. The solution was cooled to room temperature and supplemented with water for injection q.s. ad 1 l volume, giving a solution of 4 mg/ml of A.I. The solution was sterilized by filtration (U.S.P. XVII p. 811) and filled in sterile containers.

What is claimed is:

1. A compound having the formula
2 substituents selected from $C_{1-6}$alkyl, $C_{1-6}$alkyloxy, amino, mono- or di($C_{1-6}$alkyl)amino or aryl; 1-piperazinyl; 1-piperazinyl substituted with 1 or 2 substituents selected from $C_{1-6}$alkyl, $C_{1-6}$alkyloxy, amino, mono- or di ($C_{1-6}$alkyl)amino or aryl; hexahydro-1H-diazepin-1-yl or hexahydro-1H-diazepin-1-yl substituted with 1 or 2 substituents selected from $C_{1-6}$alkyl, $C_{1-6}$alkyloxy, amino, mono- or di ($C_{1-6}$alkyl)amino or aryl;

$R^5$ and $R^7$ each independently are hydrogen; $C_{1-6}$alkyl; $C_{1-6}$alkyloxy; amino; mono- or di($C_{1-6}$alkyl)amino; 1-piperidinyl; 1-piperidinyl substituted with 1 or 2 substituents selected from $C_{1-6}$alkyl, $C_{1-6}$alkyloxy, amino, mono- or di($C_{1-6}$alkyl)amino or aryl; 1-pyrrolidinyl; 1-pyrrolidinyl substituted with 1 or 2 substituents selected from $C_{1-6}$alkyl, $C_{1-6}$alkyloxy, amino, mono- or di ($C_{1-6}$alkyl)amino or aryl; 1-piperazinyl; 1-piperazinyl substituted with 1 or 2 substituents selected from $C_{1-6}$alkyl, $C_{1-6}$alkyloxy, amino, mono- or di($C_{1-6}$alkyl)amino or aryl; hexahydro-1H-diazepin-1-yl or hexahydro-1H-diazepin-1-yl substituted with 1 or 2 substituents selected from $C_{1-6}$alkyl, $C_{1-6}$alkyloxy, amino, mono- or di($C_{1-6}$alkyl)amino or aryl;

$R^6$ is hydrogen or $C_{1-6}$alkyl; and aryl is phenyl or phenyl substituted with 1, 2 or 3 substituents selected from halo, $C_{1-6}$alkyl or $C_{1-6}$alkyloxy,

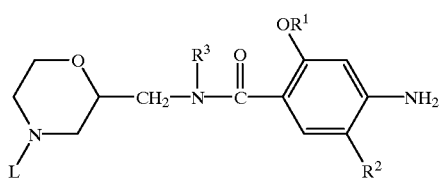

(I)

a N-oxide form, a pharmaceutically acceptable addition salt or a stereochemically isomeric form thereof, wherein $R^1$ is $C_{1-6}$alkyl, $C_{2-6}$alkenyl or $C_{2-6}$alkynyl;

$R^2$ is hydrogen, halo or $C_{1-6}$alkylsulfonylamino;

$R^3$ is hydrogen or $C_{1-6}$alkyl;

a radical of formula

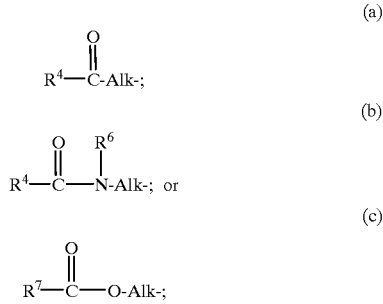

wherein each Alk independently is $C_{1-12}$alkanediyl;

$R^4$ is hydrogen; hydroxy; $C_{1-6}$alkyl; $C_{1-6}$alkyloxy, amino; mono- or di($C_{1-6}$alkyl)amino; 1-piperidinyl; 1-piperidinyl substituted with 1 or 2 substituents selected from $C_{1-6}$alkyl, $c_{1-6}$alkyloxy, amuno, mono- or di($C_{1-6}$alkyl)amino or aryl; 1-pyrrolidinyl; 1 pyrrolidinyl substituted with 1 or with the proviso that $R^4$ is other than $C_{1-6}$alkyloxy when $R^2$ is halo.

2. A compound according to claim 1, wherein $R^1$ is $C_{1-6}$alkyl.

3. A compound according to claim 1, wherein $R^2$ is halo.

4. A compound according to claim 1, wherein $R^3$ is hydrogen.

5. A compound according to claim 1, wherein L is a radical of formula (a).

6. A compound according to claim 1, wherein the compound is selected from

2-[[(4-amino-5-chloro-2-methoxybenzoyl)amino]methyl]-N,N-diethyl-4-morpholine-butanamide;

4-amino-5-chloro-2-methoxy-N-[[4-[4-oxo-4-(1-pyrrolidinyl)butyl]-2-morpholinyl]methyl]benzamide;

a pharmaceutically acceptable addition salt or a stereochemically isomeric form thereof.

7. A composition comprising a pharmaceutically acceptable carrier and, as active ingredient, a therapeutically effective amount of a compound as claimed in any one of claims 1 to 6.

8. A method of treating motility disorders of the gastrointestinal system of a warm-blooded animal comprising administering to said animal an effective amount of a compound of claim 1.

9. A method of treating motility disorders of the gastrointestinal system of a warm-blooded animal comprising administering to said animal an effective amount of a compound of claim 2.

10. A method of treating motility disorders of the gastrointestinal system of a warm-blooded animal comprising administering to said animal an effective amount of a compound of claim 3.

11. A method of treating motility disorders of the gastrointestinal system of a warm-blooded animal comprising administering to said animal an effective amount of a compound of claim 4.

12. A method of treating motility disorders of the gastrointestinal system of a warm-blooded animal comprising administering to said animal an effective amount of a compound of claim 5.

13. A method of treating motility disorders of the gastrointestinal system of a warm-blooded animal comprising administering to said animal an effective amount of a compound of claim 6.

14. A compound according to claim 2, wherein $R^2$ is halo.

15. A compound according to claim 2, wherein $R^3$ is hydrogen.

16. A compound according to claim 3, wherein $R^3$ is hydrogen.

17. A compound according to claim 14, wherein $R^3$ is hydrogen.

18. A compound according to claim 2, wherein $R^3$ is a radical formula (a).

19. A compound according to claim 3, wherein L is a radical of formula (a).

20. A compound according to claim 4, wherein L is a radical of formula (a).

21. A compound according to claim 14, wherein L is a radical of formula (a).

22. A compound according to claim 15, wherein L is a radical of formula (a).

23. A compound according to claim 16, wherein L is a radical of formula (a).

24. A compound according to claim 17, wherein L is a radical of formula (a).

25. A process for preparing a compound as claimed in claim 1, comprising N-alkylating an intermediate of formula (II) with an intermediate of formula (III)

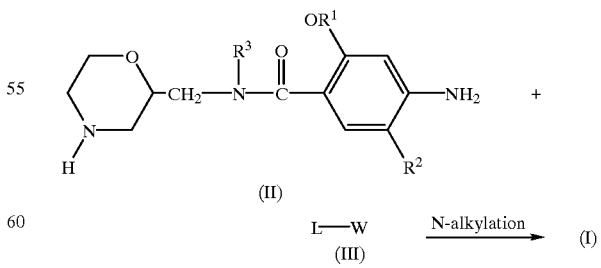

wherein W is a reactive leaving group.

* * * * *